(12) United States Patent
Harris

(10) Patent No.: US 7,322,983 B2
(45) Date of Patent: Jan. 29, 2008

(54) SELF-LOCKING BONE SCREW AND IMPLANT

(75) Inventor: Peter M. Harris, Lake Forest, CA (US)

(73) Assignee: EBI, L.P., Parsippany, NJ (US)

( * ) Notice: Subject to any disclaimer, the term of this patent is extended or adjusted under 35 U.S.C. 154(b) by 420 days.

(21) Appl. No.: 10/359,914

(22) Filed: Feb. 7, 2003

(65) Prior Publication Data

US 2003/0153919 A1    Aug. 14, 2003

Related U.S. Application Data

(60) Provisional application No. 60/356,395, filed on Feb. 12, 2002.

(51) Int. Cl.
*A61B 17/58* (2006.01)
(52) U.S. Cl. .......................................... 606/69; 606/73
(58) Field of Classification Search ............ 606/69–71; 411/307–311, 411, 426
See application file for complete search history.

(56) References Cited

U.S. PATENT DOCUMENTS

| | | | |
|---|---|---|---|
| 3,861,269 A | 1/1975 | Laverty | |
| 3,942,405 A | 3/1976 | Wagner | |
| RE28,841 E | 6/1976 | Allgower et al. | |
| RE31,628 E | 7/1984 | Allgower et al. | |
| 4,611,581 A | 9/1986 | Steffee | |
| 4,655,199 A | 4/1987 | Steffee | |
| 4,696,290 A | 9/1987 | Steffee | |
| 4,854,311 A | 8/1989 | Steffee | |
| 4,978,350 A | 12/1990 | Wagenknecht | |
| 5,006,120 A * | 4/1991 | Carter | 606/69 |
| 5,085,660 A | 2/1992 | Lin | |
| 5,147,361 A | 9/1992 | Ojima et al. | |
| 5,217,461 A | 6/1993 | Asher et al. | |
| 5,520,688 A | 5/1996 | Lin | |
| 5,601,553 A | 2/1997 | Trebing et al. | |
| 5,607,428 A | 3/1997 | Lin | |
| 5,643,261 A * | 7/1997 | Schafer et al. | 606/61 |
| 5,662,652 A * | 9/1997 | Schafer et al. | 606/61 |
| 5,709,686 A * | 1/1998 | Talos et al. | 606/69 |
| 5,738,685 A * | 4/1998 | Halm et al. | 606/61 |
| 5,797,914 A | 8/1998 | Leibinger | |
| 5,954,722 A | 9/1999 | Bono | |

(Continued)

FOREIGN PATENT DOCUMENTS

EP    0 705 572    4/1996

(Continued)

*Primary Examiner*—Eduardo C. Robert
*Assistant Examiner*—Mary Hoffman
(74) *Attorney, Agent, or Firm*—Harness, Dickey & Pierce, P.L.C.

(57) ABSTRACT

An orthopedic implant assembly is presented which has a flange member having a through bore with internal threads and a screw which has a single continuous thread that has a first section and a second section. The cross sectional configuration of the thread in the first section is different than the cross sectional configuration in the second section. The first section defines a cancellous thread while the second section defines a locking .thread which is an asymmetrical buttress thread that has the same pitch and angle along the leading or thrust surface as the cancellous thread and a thicker square spiral edge or face joined to a transverse rear surface.

11 Claims, 3 Drawing Sheets

U.S. PATENT DOCUMENTS

| | | |
|---|---|---|
| 6,017,345 A | 1/2000 | Richelsoph |
| 6,030,389 A * | 2/2000 | Wagner et al. ................. 606/71 |
| 6,074,391 A | 6/2000 | Metz-Stavenhagen et al. |
| 6,077,013 A * | 6/2000 | Yamamoto et al. ......... 411/386 |
| 6,129,730 A | 10/2000 | Bono et al. |
| 6,290,703 B1 * | 9/2001 | Ganem ......................... 606/73 |
| 6,468,277 B1 * | 10/2002 | Justin et al. ................... 606/65 |
| 6,503,252 B2 * | 1/2003 | Hansson ....................... 606/73 |
| 6,575,975 B2 * | 6/2003 | Brace et al. ................... 606/69 |
| 6,585,740 B2 * | 7/2003 | Schlapfer et al. ............. 606/73 |
| 6,595,993 B2 * | 7/2003 | Donno et al. ................. 606/71 |
| 6,602,256 B1 * | 8/2003 | Hayes .......................... 606/69 |
| 6,730,091 B1 * | 5/2004 | Pfefferle et al. ............... 606/70 |
| 2003/0187442 A1 * | 10/2003 | Richelsoph et al. .......... 606/70 |
| 2004/0172028 A1 * | 9/2004 | Roger .......................... 606/69 |

FOREIGN PATENT DOCUMENTS

| | | |
|---|---|---|
| FR | 742618 | 3/1933 |
| FR | 2 739 151 | 3/1997 |
| WO | WO 00/28905 | 2/2000 |
| WO | WO 00/66011 | 11/2000 |
| WO | WO 01/01874 | 1/2001 |
| WO | WO 01/12081 | 2/2001 |

* cited by examiner

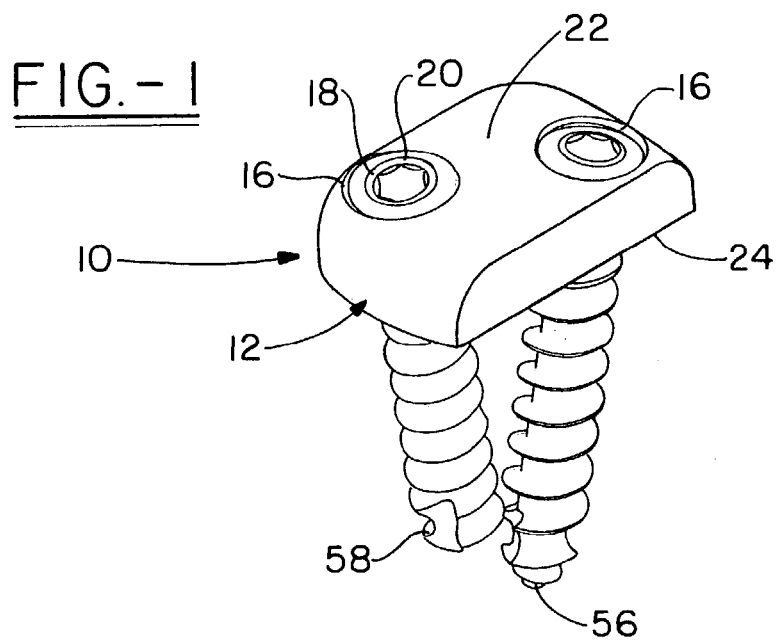
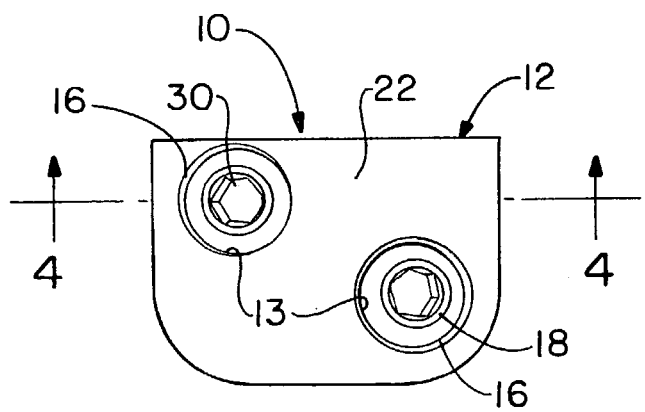
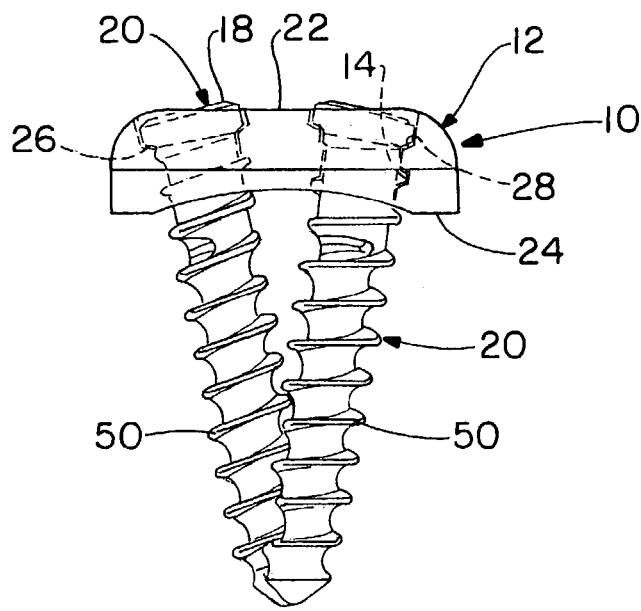

SELF-LOCKING BONE SCREW AND IMPLANT

This Patent Application is Based Upon U.S. Provisional Application Ser. No., 60/356,395, Filed Feb. 12, 2002

The present invention relates to an orthopedic implant and a mating bone screw which locks in position in a threaded through bore in the implant. In particular, the screw has a continuous thread having a leading surface that has one constant pitch throughout the length of the screw. However the single thread has two sections each having their own thread configuration. From the tip end the first area of thread comprises a cancellous screw thread which is designed for engagement of the bone whereas the second, shorter area near the distil end is modified to form the locking thread having the same angle as for the first section of thread on the leading edge or thrust surface, but having a different angle than the first section on the rear surface. The locking thread also has a truncated peripheral edge as compared to the first thread section to define a thicker spiral surface or face. In addition, while the thread has the same major diameter throughout the entire length of the continuous thread, the locking area has a larger minor diameter than the cancellous region.

BACKGROUND OF THE INVENTION

Orthopedic implants include numerous structures that are implanted into a living body in order to augment or supplant the bone structure of the patient into whom it is implanted. For example, such implants can include plate structures that act to stabilize broken bones during the healing process. They can also include vertebral cages or vertebral inter-body spacers that maintain the relative position of the vertebrae during fusion. Implants can also include constructs such as mesh that is used to maintain fragments in position or rod systems that are used to align and position the vertebrae. The present invention can be used with any such implant so long as it includes a portion having a through bore adjacent a bottom surface that opposes the bone to which the implant is anchored. In general, although not necessarily exclusively, this portion will have a bottom bone engaging surface, and an opposing top surface (top and bottom being defined relative to the bone surface that engages the implant) defining a thickness in between to form a plate like area which includes the threaded through bore.

One problem that may be encountered with implants that are fastened to the bone using a screw is that there may be too much play between the screw and the implant, or that the screw may back out of the implant. Of course, the implant forms part of a dynamic system with the skeletal structure, and is subject to constant and varied forces. Locking mechanisms help to ensure that the screw does not back out of the plate. If a screw backs out of an implant depending on the placement there may be a risk that it may project beyond the top surface of the implant into a sensitive biological area. This raises the possibility of irritation to adjoining soft tissue. Another possibility if there is too much movement between the plate and the screw is that the plate may play against the screw and increase the risk of shearing the screw.

Various solutions have been used to lock the screw relative to the implant. One prior art solution has been to provide the screw with a locking member such as a nut or collet that engages a portion of the screw. An additional solution has been to provide the screw with a second set of locking threads near the head of the screw. These locking threads mate with internal threads within the screw hole of the recess. However, the existence of multiple start threads can cause problems with cross threading of the male threads within the female threads of the recess during implantation. This can cause the screw to become irreparably stuck in the implant, able to travel neither into nor out of the bore. While this problem would be at least frustrating in the context of a static bracket such as for example, a wall anchor, the surgical context and difficulties in accessing the site, as well as the time concerns increase the complications with such problems considerably. Often a surgeon is working a substantial distance, like 5-15 inches through an incision to the bone implantation site, the area is cramped, visibility is obscured, and timing is critical.

The present invention provides a very elegant solution to the locking problem which enjoys a minimum of component parts, and which neatly locks the screw in the implant while avoiding prior art problems of cross threading of the locking threads with the mating locking threads of the plate.

SUMMARY OF THE INVENTION

The present invention relates to an orthopedic implant having an internally threaded recess that receives the external threads of a screw that fastens the implant to a bone portion. The screw has external threads that form two distinct areas or sections of thread along the longitudinal length of the screw wherein the thread has a different cross section for each of the areas. The first area is a bone engaging area which has a buttress configuration known in the art as a cancellous thread. The threads of the first area have a single continuous pitch and have a cross sectional shape that is generally known as a cancellous thread. This is a specific type of buttress thread having a front thrust surface that forms an angle of about 20-30, and more preferably about 22-26 degrees with respect to a line that is perpendicular to the longitudinal axis of the screw.

As used herein, buttress thread refers to a thread designed to withstand heavy axial thrust in one direction, often the back of the thread slopes (for example, at 45°) while the front or thrust face is perpendicular to the axis. The present "cancellous" configuration is designed specifically for use in anchoring in bone (including the cortical and cancellous areas) and generally has an asymmetrical thread cross section with a front leading edge or "thrust surface" which has a portion at an angle of about 24° relative to a line perpendicular to the longitudinal axis of the screw. The rear surface of the thread (relative to the direction of insertion) has a portion which is substantially parallel to the previously mentioned perpendicular line. The thrust surface also includes a radiused or curving portion that blends into the minor diameter of the screw in order to cause compression of the bony material. This cancellous area preferably extends over the majority of the length of the screw, depending on the length of the screw and the application of the implant.

The second area of threads is a locking area that preferably extends over a length that generally corresponds to the length of the mating threads within a recess in the implant. Moreover, the female threads of the recess generally correspond in outline to the mating male threads of the locking section within generally accepted tolerances. Thus, the female thread has a leading surface at an angle of about 24°, maintaining the same leading angle and pitch for both the female threads and the male threads of the locking section as for the cancellous section. The pitch is defined as the length, measured along the longitudinal axis, of a complete turn of the thread of a screw, measured from face to face of any two adjacent threads. The locking thread also has a rear surface which is substantially perpendicular to the longitudinal axis of the recess. This contrasts in profile to the shape of the cancellous thread rear surface. In addition, this area has a larger minor diameter, while maintaining the same major diameter of the thread. The term minor diameter refers to the cylindrical core at the inside of the screw, while the term major diameter refers to the diameter taken at the spiral edge of the screw or at the edge of the flight. Further, the locking threads have a squared spiral edge or face which increases the thickness of the material comprising the thread. The threaded recess of the implant has a flight depth from the minor axis to the major axis which is slightly larger than that of the male screw (i.e., having a difference in the order of about 0.001 to about 0.005 inch or more.) Likewise the screw has a spiral edge which is slightly larger than the depth of the spiral edge of the locking thread. The continuation of the front pitch, and of the same major diameter allows the screw to be smoothly screwed through the implant recess from the first section of threads into the second locking section. This avoids the prior problems associated with interference in this smooth motion that may result in cross threading problems. However, the increase in the minor diameter, the increase in the depth of the face and the change in the rear edge to a substantially perpendicular (+/−5°) surface increase the stability of the screw by decreasing the possibility of material failure of the screw, and increasing the stability of the screw in the recess by causing it to lock into place when the bottom of the screw head finally rests against the bottom of the counter sink area of the recess which receives the screw head. Thus, the rear face of the screw thread has the same pitch in a first longitudinal section and a second longitudinal section; however, the pitch of the rear face increases at the junction of the first and second section, i.e. the transition area. In this area the minor diameter increases. The threads run out very near the head for the screw and near the top of the countersink so that the head of the screw is nearly flush with the surface of the implant. There is some allowable axial play between the cancellous portion of the screw and the female mating thread. This is to allow for some correction when inserting the self-tapping bone screws, in the event that the implant shifts after the initial guide holes have been drilled.

In addition, the first section of the screw includes a fluted cutting section where the thread preferably runs to the insertion tip. The second section has a terminal head which includes a rounded top surface to avoid any irritating projections. The head includes an internal hexagon to permit the screw to be threaded into the recess.

The continuous pitch locking screw of the present invention is illustrated with a substantially co-planar implant that could be a plate, or could be a flange of a vertebral cage. In addition, it is noted that two screws are used in the implant, and are angled inwardly toward each other, such as at an angle of from about 5 about 15 degrees, and preferably around 10 degrees from the vertical. The recesses are accordingly angled to accommodate the desired degree of angulation. A threaded drill guide is screwed into the implant and is used to drill the initial guide holes in the bone, (and to continue to insert the screws at the proper angle and correct trajectory.)

BRIEF DESCRIPTION OF THE DRAWINGS

FIG. 1 is an isometric view of the implant and locking screws in accordance with the present invention;

FIG. 2 is an end view of the implant and of FIG. 1;

FIG. 3 is a top view of the implant and locking screws of FIG. 1;

DETAILED DESCRIPTION OF THE INVENTION

Figure 4:
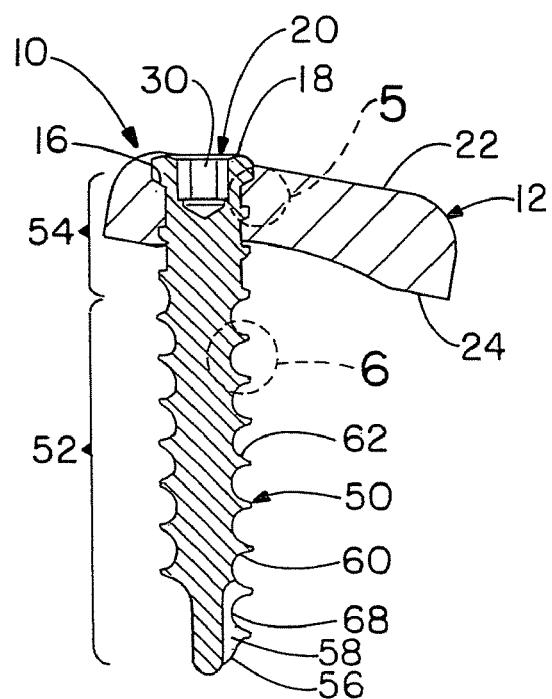
FIG. 4 is a cross section of the implant and locking screw of FIG. 1 taken along line 4-4 of FIG. 3.
Figure 5:
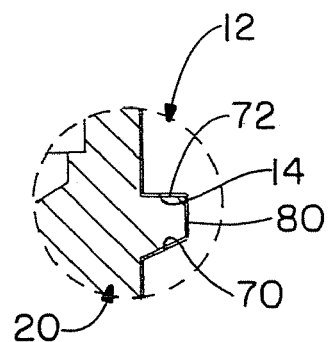
FIG. 5 is a detail of the locking thread shown in FIG. 4.
Figure 6:
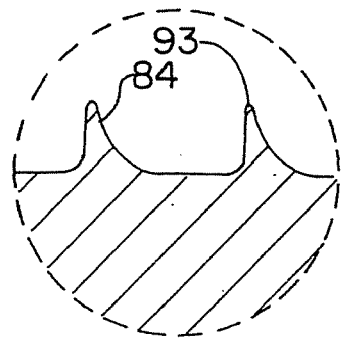
FIG. 6 is a detail of the cancellous thread shown in FIG. 4.
Figure 7:
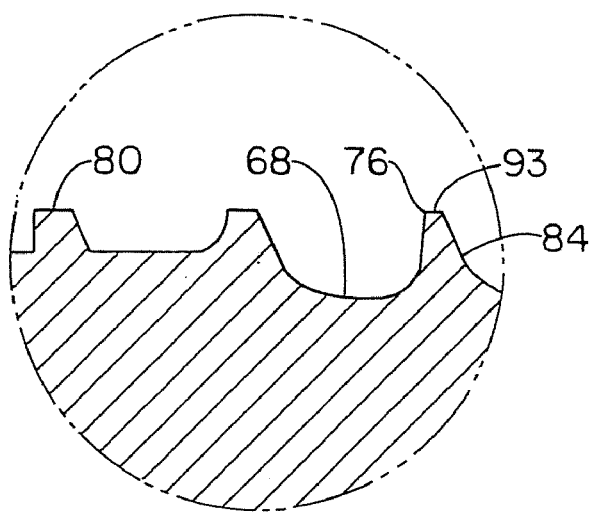
FIG. 7 illustrates a detail of the transition area between the first section of cancellous thread and the second locking-thread section. The major diameter remains the same while the minor diameter changes.

The present invention relates to an orthopedic implant assembly shown generally at 10 and including an implant 12 having at least one through bore 13 which includes internal or female threads 14. The bore 13 has an opening at the top with a countersunk area 16 which is configured so that the circular head 18 of a corresponding screw 20 will be mostly recessed within the bore 13 and will have only minimal projection beyond the top surface 22 of the implant surrounding the opening. In addition, the head 18 has a rounded top surface to help accomplish this goal. In addition, the implant 12 is shown as having two opposing surfaces (i.e. top 22 and bottom 24 relative to the bone surface) defining a thickness between. The bottom surface 24 is shown in this case, as having a curve to better fit the corresponding bone engaging surface. Further, the head 18 has a bottom bevel 26 that rest against a beveled recess 28 in the countersunk area 16 so as to secure the screw 20 in place. Also the screw includes an internal torque driving recess 30 that is shown as an internal hexagon but can include other torque driving shapes such as a key, torx or multi-lobe shape. As shown, the implant has multiple screw passages or through bores 13 and is illustrated with two passages 13 that are angled at a slope of from about 5 to about 15 degrees to a vertical line relative to the top surface of the implant. Further, the passages are offset with respect to a lateral axis of the implant in order to avoid conflict between the screws at the tips.

The screw 20 of the present invention includes a thread which is preferably a single continuous thread 50 having two regions or sections 52,54 along the longitudinal length of the screw that have differing thread configurations. Preferably, the thread runs out to an insertion tip 56 which further may include one or more flutes 58 so that the screw is self-tapping. In addition, the thread runs to the distal end having the head 18.

While the thread is preferably a single continuous thread, that changes configuration to form two distinct areas or sections of thread along the longitudinal length of the screw. Thus, the thread has a different cross section for each of the areas. The first area 52 is a bone engaging area which has a buttress configuration known in the art as a cancellous thread. The threads this area have a single continuous pitch (or rise and run) and have a cross sectional shape that is generally known as a cancellous thread. This is a specific type of buttress thread having a front thrust surface 60 that forms an angle of about 20-30 degrees, and more preferably about 22-26 degrees with respect to a line that is perpendicular to the longitudinal axis of the screw. The "front thrust surface" as used herein refers to the spiraling surface which extends outward and leads during screwing of the screw into the through bore 13. The rear surface 62 of the thread (relative to the direction of insertion) has a portion which is substantially parallel to the previously mentioned perpendicular line. The thrust surface also includes a radiused or curving portion 84 that blends into the minor diameter 68 of the screw in order to cause compression of the bony material. There is a flat on the thread surface which defines the major diameter surface 76. This area of cancellous thread 93 preferably extends over the majority of the length of the screw, depending on the length of the screw and the application of the implant.

The second area of threads 54 forms a locking area that preferably extends over a length that generally corresponds to the length of the mating threads or female threads 14 within the through bore 13. These female threads 14 generally correspond in outline to the mating male threads of the locking section within generally accepted tolerances. Thus, the female thread 14 has a leading surface 70 at an angle of about 24° degrees, maintaining the same leading angle and pitch for both the female threads 14 and the male threads 50 of the locking section 54 as for the cancellous section 52. The locking thread 54 also has a rear surface 72 which is substantially perpendicular to the longitudinal axis of the recess. This contrasts in profile to the shape of the cancellous thread rear surface 62. In addition, this area 54 has a larger minor diameter 74, while maintaining the same major diameter 76 of the thread 50. Further, the locking threads 54 have a squared spiral edge or face 80 which increases the thickness of the material comprising the thread. The female thread and the male locking thread 54 have a general correspondence within standard tolerances.

The implant is made from generally acceptable implantable materials such as surgical grade stainless steel or titanium, or from composite materials, including for example carbon composites. Generally, all of the components are made from the same material.

While in accordance with the patent statutes the best mode and. preferred embodiment have been set forth, the scope of the invention is not limited thereto, but rather by the scope of the attached claims.

What is claimed is:

1. An orthopedic implant assembly comprising an implant having at least one through bore having internal threads and a screw which has a longitudinal axis and having only one single continuous screw thread having a first section and a second section which describes a spiral defining a pitch along the longitudinal axis, and the first section and the second section have a major diameter which is the same, and the first section has a first minor constant diameter extending through the first section and the second section has a second constant minor diameter extending through the second section, and the first minor diameter is smaller than the second minor diameter, and wherein the screw thread has a cancellous configuration along the first section and a locking configuration along the second section, and wherein the thread has a leading face along the spiral which has the same pitch for the first section and the second section, wherein the screw thread has a rear surface and there is a transition area between the first and second section and wherein the rear surface of the screw thread has the same pitch in the first and second section, and wherein the pitch of the rear surface increases in the transition area.

2. An orthopedic implant assembly as set forth in claim 1 wherein the screw thread has a continuous spiral edge which is thinner in the first section than in the second section.

3. An orthopedic implant assembly as set forth in claim 2 wherein the screw thread has a leading surface which defines an angle to the longitudinal axis of the screw and wherein the angle of the leading surface of the screw thread is the same for the first section and the second section.

4. An orthopedic implant assembly as set forth in claim 3 wherein the rear surface of the screw thread defines an angle relative to the longitudinal axis of the screw and the angle of the rear surface of the screw thread in the first section is different than the angle of the screw thread in the second section, and the angle of the screw thread in the second section is from about 85 to about 95 degrees to the longitudinal axis.

5. An orthopedic implant assembly as set forth in claim 4 wherein the at least one through bore has a countersunk area, and the screw has a head which resides in the countersunk area when the locking threads of the second section fully mate with the internal threads of the through bore.

6. An orthopedic implant assembly as set forth in claim 1 wherein the implant is a plate.

7. An orthopedic implant assembly as set forth in claim 1 wherein the implant has a flange which includes the at least one through bore.

8. An orthopedic implant assembly as set forth in claim 1 wherein the implant has a bottom surface which is adapted to face the bone and an opposing top surface, and the through bore has a longitudinal axis that is at an angle other than 90 degrees relative to the top surface of the implant.

9. An orthopedic assembly as set forth in claim 8 wherein the screw has a head having a diameter which is greater than the major diameter and the at least one through bore has a counter sunk area.

10. An orthopedic implant assembly as set forth in claim 1 wherein the leading surface of the cancellous configuration has a given pitch which forms an angle of from about 20 to about 30 degrees to a line perpendicular to the longitudinal axis and the locking configuration has the given pitch and the same angle as the cancellous configuration and wherein the rear surface of the cancellous configuration is at an angle of about 0 to about 5 degrees to the line perpendicular to the longitudinal axis and the rear surface of the locking configuration has an angle of from about 0 to about 5 degrees to the line perpendicular to the longitudinal axis and wherein the screw thread has a spiral edge of a first thickness in the first section and a spiral edge of a second thickness in the second section and the second thickness is greater than the first section and the spiral edge in the second section is at an angle of about 85 to 95 degrees to the rear surface in the second configuration.

11. An orthopedic implant assembly as set forth in claim 10 wherein at least one through bore has a countersunk area that has a terminal bevel that leads into the at least one through bore and a head of the screw has a bevel that mates with the bevel of the countersunk area.

* * * * *